US008879058B2

United States Patent
Murugkar et al.

(10) Patent No.: US 8,879,058 B2
(45) Date of Patent: Nov. 4, 2014

(54) MINIATURIZED MULTIMODAL CARS ENDOSCOPE

(75) Inventors: Sangeeta Murugkar, Ottawa (CA); Peter K. Stys, Calgary (CA); Hanan Anis, Kanata (CA)

(73) Assignee: The University of Ottawa, Ottawa (CA)

( * ) Notice: Subject to any disclaimer, the term of this patent is extended or adjusted under 35 U.S.C. 154(b) by 237 days.

(21) Appl. No.: 13/289,770

(22) Filed: Nov. 4, 2011

(65) Prior Publication Data

US 2012/0281211 A1 Nov. 8, 2012

Related U.S. Application Data

(60) Provisional application No. 61/410,556, filed on Nov. 5, 2010.

(51) Int. Cl.
| | |
|---|---|
| *G01J 3/44* | (2006.01) |
| *G01J 3/10* | (2006.01) |
| *G02B 23/24* | (2006.01) |
| *G01J 3/02* | (2006.01) |
| *A61B 1/00* | (2006.01) |
| *A61B 1/06* | (2006.01) |
| *A61B 1/07* | (2006.01) |

(52) U.S. Cl.
CPC ...... *G01J 3/44* (2013.01); *G01J 3/10* (2013.01); *G02B 23/2446* (2013.01); *G01J 3/0208* (2013.01); *A61B 1/00165* (2013.01); *A61B 1/00172* (2013.01); *A61B 1/0638* (2013.01); *A61B 1/0646* (2013.01); *A61B 1/063* (2013.01); *A61B 1/07* (2013.01)
USPC ........................................................ 356/301

(58) Field of Classification Search
CPC .. A61B 1/0019; A61B 1/002; A61B 1/00165; A61B 1/00172; A61B 1/063; G02B 23/243; G02B 23/2446

USPC .................. 356/301, 300, 321, 309, 332; 600/100–183
See application file for complete search history.

(56) References Cited

U.S. PATENT DOCUMENTS

| | | | | |
|---|---|---|---|---|
| 4,655,557 A | * | 4/1987 | Takahashi | 359/735 |
| 4,918,301 A | * | 4/1990 | Miyatake | 250/216 |
| 4,964,686 A | * | 10/1990 | Kato | 359/423 |

(Continued)

OTHER PUBLICATIONS

Sanjeev Dutta, "Transaxillary subcutaneous endoscopic release of the sternocleidomastoid muscle for treatment of persistent torticollis", 2008.*

(Continued)

*Primary Examiner* — Kara E Geisel
*Assistant Examiner* — Maurice Smith
(74) *Attorney, Agent, or Firm* — Harness, Dickey & Pierce, P.L.C.

(57) ABSTRACT

A miniaturized imaging system is provided that operates in multiple modes, including a coherent anti-stokes Raman scattering (CARS) mode. The imaging system includes: a laser delivery subsystem that generates an excitation signal; a scanning mechanism configured to receive the excitation signal from the laser delivery subsystem and direct the excitation signal through an optics subsystem onto a sample, such that the optics subsystem compensates for chromatic aberration in the excitation signal; and a dichroic mirror that receives emission from the sample in a backward direction and directs the emission along a collection path to a detector. The light source for the laser delivery subsystem may be a single femtosecond pulse laser.

18 Claims, 5 Drawing Sheets

(56) References Cited

U.S. PATENT DOCUMENTS

| | | | |
|---|---|---|---|
| 6,853,485 B2* | 2/2005 | Hoogland | 359/435 |
| 6,860,605 B2* | 3/2005 | Blei et al. | 353/31 |
| 6,913,686 B2* | 7/2005 | Hilgarth | 205/788.5 |
| 7,170,061 B2* | 1/2007 | Clarke et al. | 250/361 R |
| 7,307,774 B1* | 12/2007 | Schnitzer et al. | 359/290 |
| 7,324,272 B1* | 1/2008 | Deck | 359/385 |
| 7,414,729 B2* | 8/2008 | Xie et al. | 356/484 |
| 2006/0175545 A1* | 8/2006 | Lee et al. | 250/234 |
| 2008/0059135 A1* | 3/2008 | Murugkar et al. | 703/11 |
| 2008/0291443 A1* | 11/2008 | Malinovskaya et al. | 356/301 |
| 2009/0060381 A1* | 3/2009 | Dunki-Jacobs | 382/275 |

OTHER PUBLICATIONS

D.R. Snelling, "Single pulse CARS noise: a comparison between single-mode and multimode pump lasers", Sep. 1, 1985.*

S. Murugkar et al., "Coherent Anti-Stokes Raman Scattering Microscopy Using Photonic Crystal Fiber With Two Closely Lying Zero Dispersion Wavelengths", vol. 15, No. 21/ Optics Express 14028, Oct. 17, 2007.

* cited by examiner

MINIATURIZED MULTIMODAL CARS ENDOSCOPE

CROSS-REFERENCE TO RELATED APPLICATIONS

This application claims the benefit of U.S. Provisional Application No. 61/410,556, filed on Nov. 5, 2010. The entire disclosure of the above application is incorporated herein by reference.

FIELD

The present disclosure relates generally to a miniaturized multimodal endoscope having a coherent anti-stokes Raman scattering (CARS) mode.

BACKGROUND

Coherent anti-stokes Raman scattering (CARS) microscopy has evolved over the past decade as a powerful label-free imaging modality based on intrinsic vibrational contrast. A wide variety of important applications involving CARS microscopy have been demonstrated. These range from imaging lipid droplet biology, imaging axonal myelin in spinal cord injuries and demyelinating diseases, identifying obesity related risks in cancer and atherosclerosis and the rapid detection of pathogens. Moreover, it has been clearly shown that there is a tremendous benefit in combining CARS with other imaging modalities, such as two photon excitation fluorescence (TPEF), second harmonic generation (SHG), and third harmonic generation (THG) in a multimodal imaging and spectroscopy platform to obtain a complete picture of the health of the biological tissue. However, in order to truly extend the benefits of multimodal CARS microscopy to human health, development of a multimodal CARS probe in the form of an endoscope or miniaturized hand held microscope is essential. In fact, significant progress has been made in the development of TPEF and SHG imaging endoscopes and miniaturized microscopes for in vivo imaging applications. For CARS microscopy which involves the pump and Stokes beams for excitation of the nonlinear optical signal, progress towards fiber based endoscopy has been quite slow. The key challenges have been (i) the efficient delivery of the ultrafast pump and Stokes light using optical fibers (ii) efficient fiber based collection of the CARS signal (iii) miniaturization of laser scanning mechanisms and (iv) efficient design of chromatic aberration corrected miniature optics for achieving high resolution CARS images. Past research efforts have focused mostly on overcoming the challenges of fiber based light delivery and collection. In particular, laser scanning and focusing at the sample to generate a CARS image was achieved using standard macro-optics, such as a galvanometric scanner and a microscope objective. Only recently, progress was reported related to the design and modeling and implementation of a fiber scanning based CARS endoscope.

Therefore, it is desirable to develop a miniaturized multimodal CARS endoscope. This section provides background information related to the present disclosure which is not necessarily prior art.

SUMMARY

A miniaturized imaging system is provided that operates in multiple modes, including a coherent anti-stokes Raman scattering (CARS) mode. The system includes: a laser delivery subsystem that generates an excitation signal; a scanning mechanism configured to receive the excitation signal from the laser delivery subsystem and direct the excitation signal in a given direction towards the sample; an optics subsystem configured to receive the excitation signal from the scanning mechanism and operates to focus the excitation signal onto the sample; and a dichroic mirror that receives emission resulting from non-linear interaction of the excitation signal with the sample and direct the emission along a collection path to a detector. In addition to a CARS mode, different operating modes of the probe may include a second harmonic generation mode, a third harmonic generation mode and a two photon excitation fluorescence mode.

In one aspect, the light source for the laser delivery subsystem may be implemented using a single femtosecond pulse laser.

In another aspect, the scanning mechanism may be further defined as a mirror actuated in a micro-electro-mechanical system.

In another aspect, the optics subsystem compensates for chromatic aberration in the excitation signal and may be comprised of a field lens and a front end objective lens, each lens comprised of at least two different types of glass to compensate for chromatic aberration.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

Figure 4:
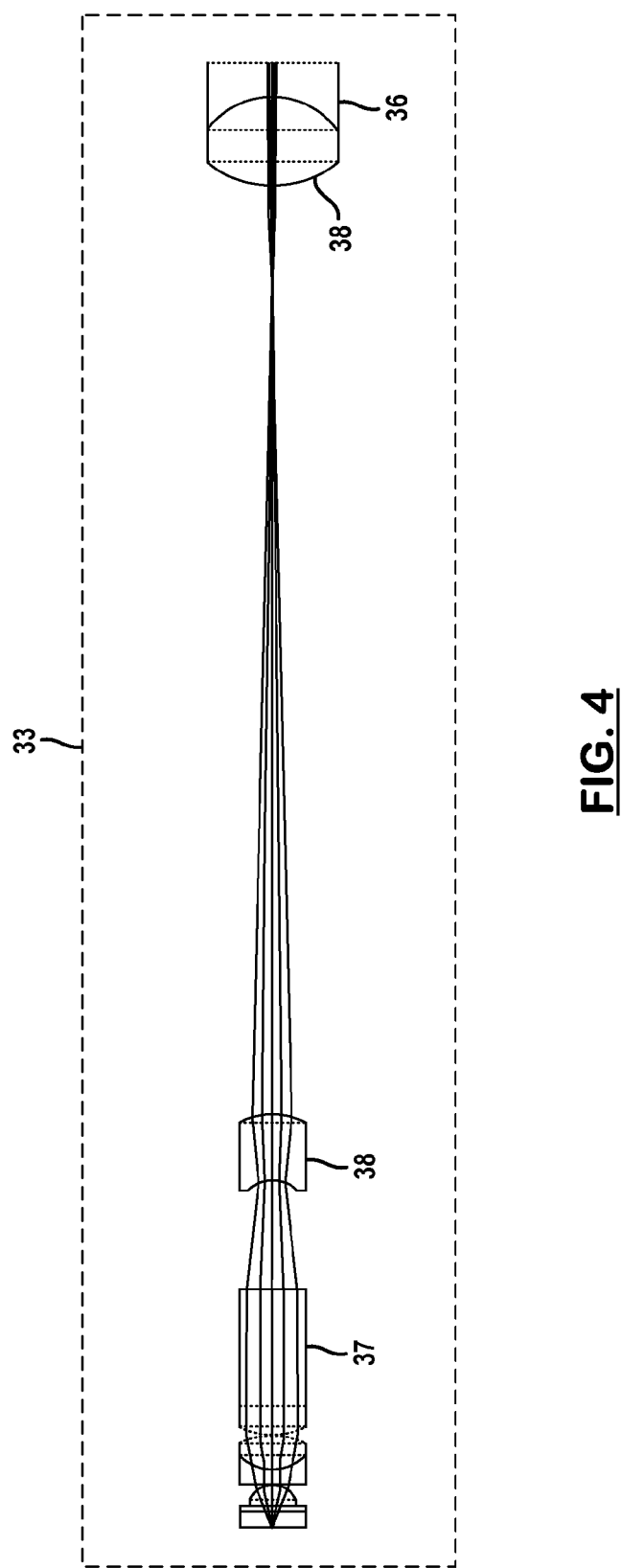
Figure 5:
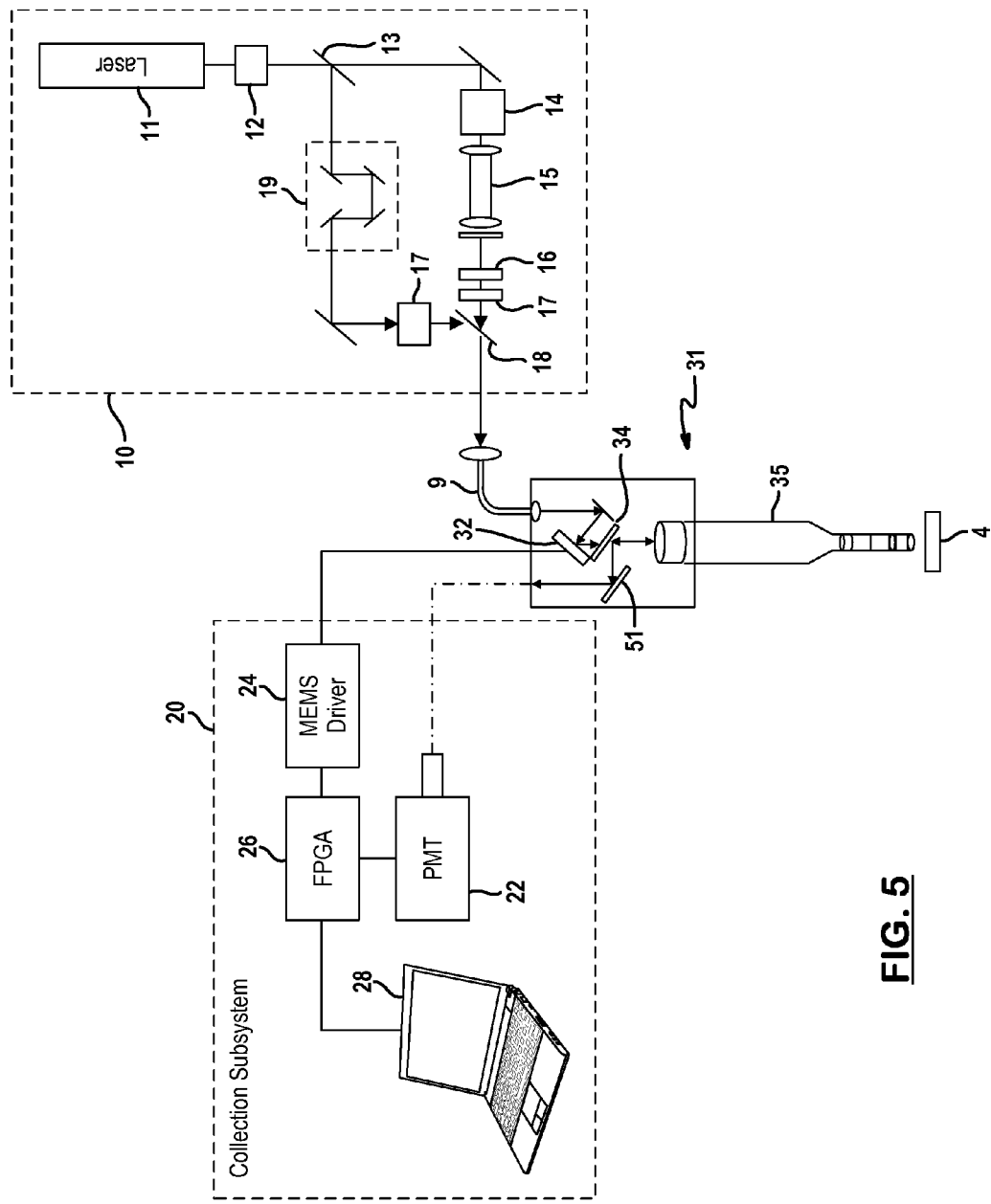

FIG. 4 is a ray-trace diagram of the optical beam propagating through the optics subsystem of the endoscope system; and FIG. 5 is a block diagram depicting components of the multimodal endoscope system in another exemplary embodiment; and The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Figure 1:
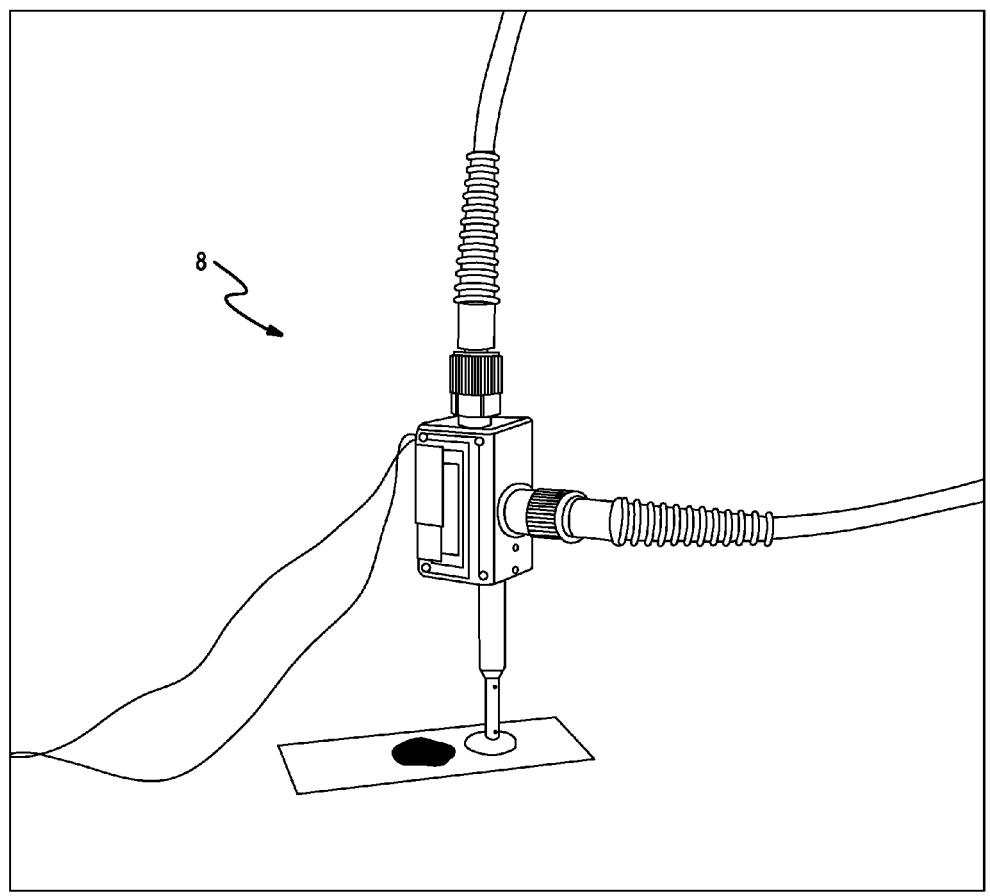
FIG. 1 depicts an exemplary handheld multimodal probe.
Figure 2:
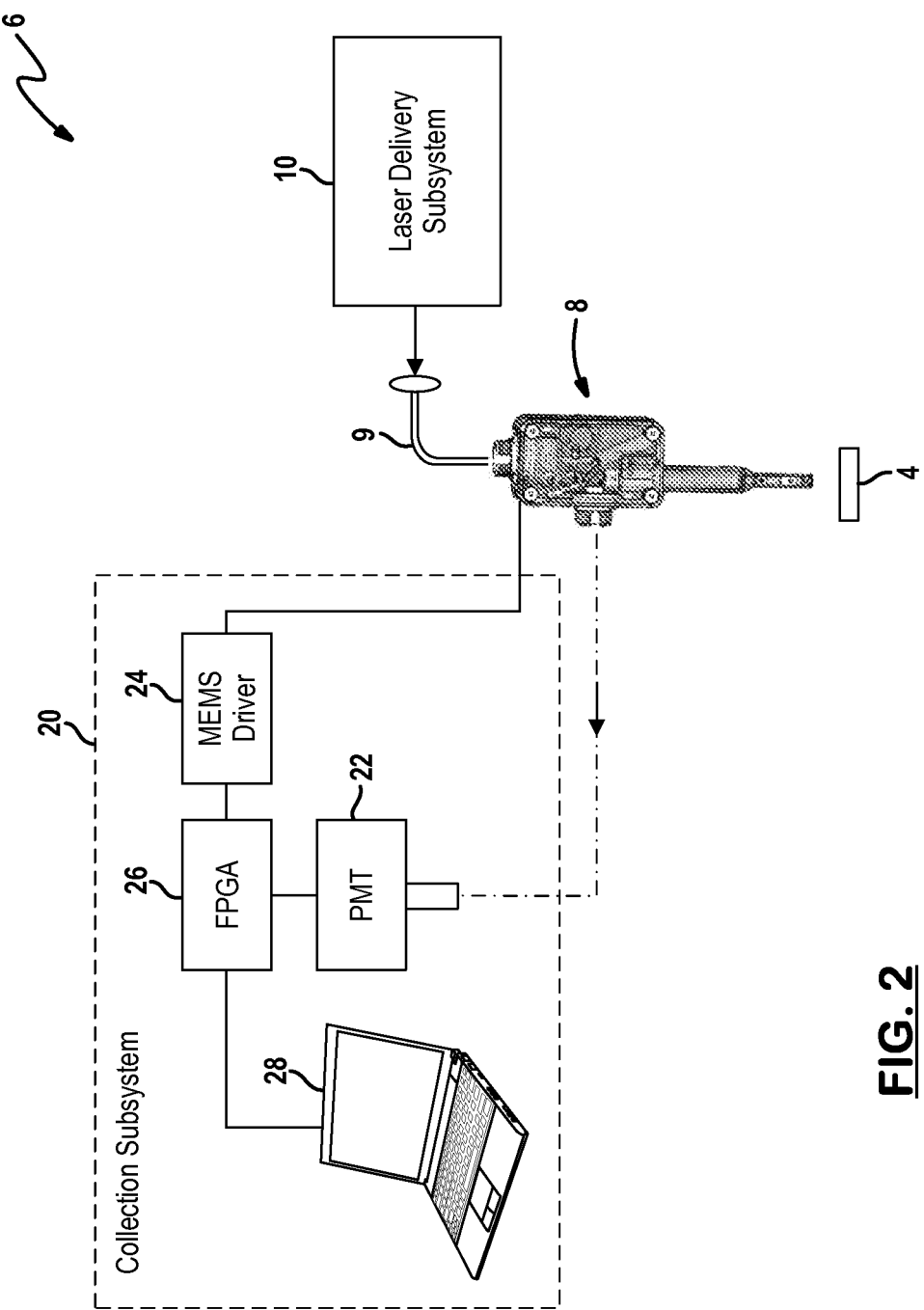
FIG. 2 is a diagram of a multimodal endoscope system.

FIG. 1 depicts an exemplary handheld imaging probe 8 which has been designed to obtain high resolution and distortion-free images from various samples including but not limited to USAF targets, fluorescent and polystyrenes microspheres and biological tissues. During operation, the probe 8 may be grasped by the user and positioned proximate to the sample of interest. Alternately, the probe 8 can be screw-mounted onto a stand fixed to a table. In any case, the probe 8 may operate as part of a multimodal endoscope system 6 as shown in FIG. 2. It is understood that the probe can be generalized to a portable probe or could be inserted inside a catheter. While the following description makes reference to an endoscope system, the system can be implemented as a microscope system or generalized as an imaging system.

The multimodal endoscope system 6 is comprised generally of a laser delivery subsystem 10, the handheld probe 8 and a data collection subsystem 20. The laser delivery subsystem 10 generates an excitation signal that is delivered optically via an optical fiber 9 to the handheld probe 8. The handheld probe 8 in turn directs the excitation signal towards a sample 4. The collection subsystem 20 is configured to process image data received from the sample 4. Each of these subsystems will be further described below.

Figure 3:
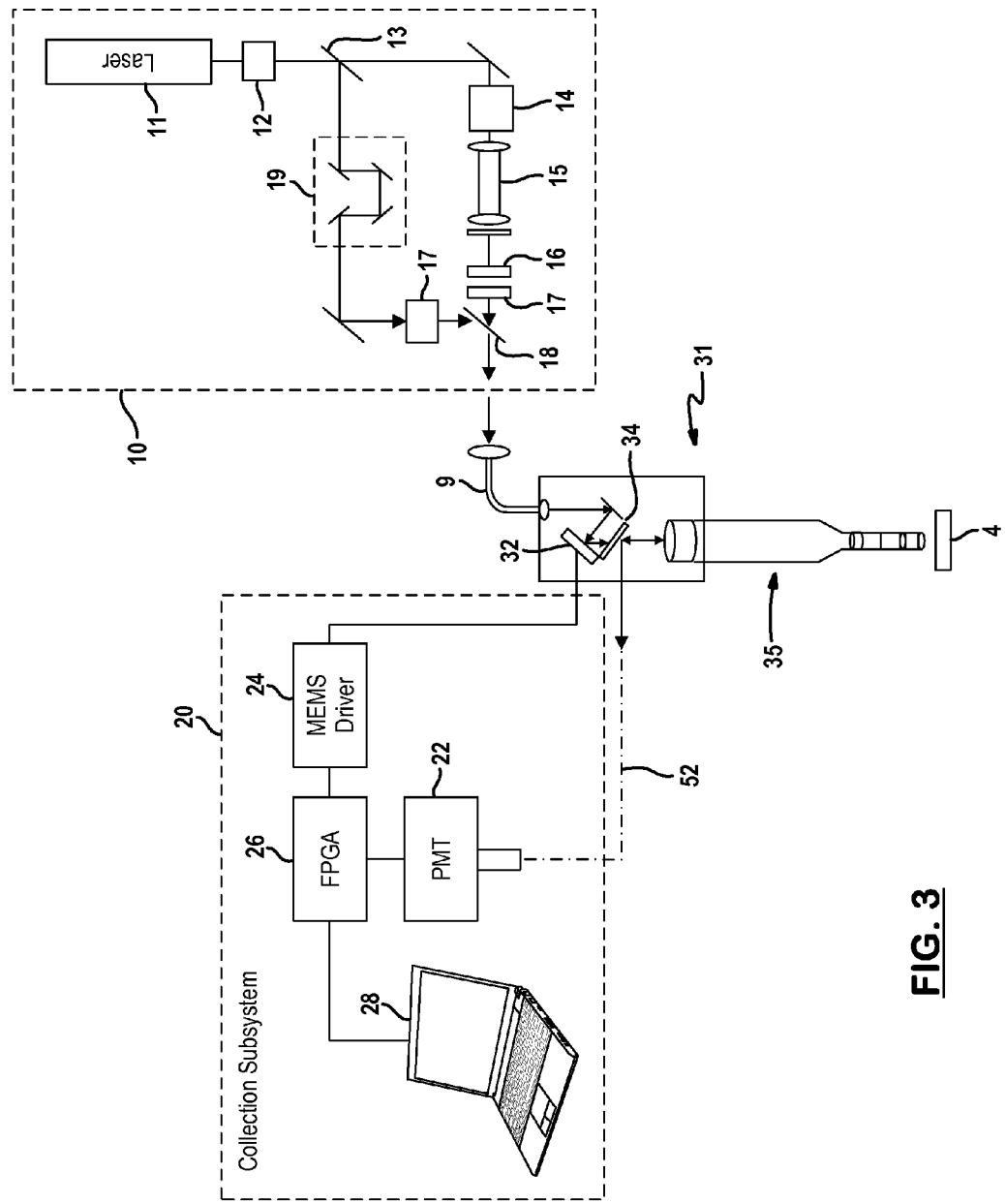
FIG. 3 is a block diagram depicting components of the multimodal endoscope system in an exemplary embodiment.

With reference to FIG. 3, the laser delivery subsystem 10 can generate an excitation signal using a single laser light source 11. In one exemplary embodiment, the light source is further defined as a single titanium sapphire laser producing ~65 femtosecond pulses at 80 MHz repetition rate and tunable between 720 nm-1000 nm. Such lasers are commercially available, for example, the Tsunami laser from Spectra-Physics in Mountain View, Calif. although other types of light sources are contemplated. While reference is made to a single light source arrangement, it is understood that the excitation signal may be generated from a synchronized programmable laser, two of the same or different synchronized lasers, such as a femtosecond laser for pump and a picosecond laser for Stokes or some other combination of lasers and optical parameteric amplifier (OPA) or optical parameteric oscillator (OPO).

Light from the laser source 11 is directed to a flip mirror 13 or some other selective beam splitting component. The flip mirror 13 is operable is one of two configurations. In a standard (or pump only) configuration, the flip mirror 13 functions as a mirror that directs the light along a pump path. In a CARS configuration, the flip mirror functions as a beam splitter that divides the light into a pump beam traveling along a pump path and a Stokes beam traveling along a Stokes path as shown in FIG. 3. In the exemplary embodiment, about 300 mW of the light is partitioned to the Stokes path while the remainder of the light (~400 mW) is partitioned to the pump path. The light from the laser source 11 may pass through a Faraday isolator 12 before reaching beam splitter 13. In either mode, the light output by the laser delivery subsystem is referred to as the excitation signal.

To create a Stokes beam, light in the Stokes path passes through a photonic crystal fiber (PCF) 15, such as the FemtoWhite CARS fiber commercially available from NKT Photonics. In one exemplary embodiment, the supercontinuum output from the PCF 15 is band pass filtered so that it consists of wavelengths between 1014 nm-1067 nm. In another embodiment, a long pass filter that transmits wavelengths above a certain wavelength, such as 900 nm, may be used in instead of the band pass filter. A prism compressor 14 may be disposed before the PCF 14 to shorten the duration of the positively chirped laser pulses incident on the PCF. In the pump path, the pump beam passes through a computer controlled delay stage 19 which serves to overlap the pump beam and the Stokes beam in time at the sample. In the exemplary embodiment, a dichroic mirror 18 is used to combine the pump beam with the Stokes beam to form the excitation signal although other optical combining components are contemplated by this disclosure.

Prechirp units 17 may be disposed in the pump path and Stokes path, respectively. The prechirp units 17 compensate for the dispersion that will broaden the pump and Stokes pulses as they propagate through the fiber as well as the various elements of the probe. A linear chirp element 16 may also be introduced in the Stokes path in order to control the spectral resolution of the device. Lastly, a telescope could be included in the pump or Stokes paths to increase coupling efficiency of the excitation signal into the optical fiber delivery system 9.

For each operating mode (i.e., CARS, SHG, THG, TPEF, etc.), the laser source 11 can be tuned to a particular wavelength. Depending upon the sample and other factors, the particular wavelength may be the same or different amongst the operating modes. In one example embodiment of the CARS mode, the frequency difference between the pump and anti-Stokes beams is tuned to a CARS frequency of 2840 cm−1+\−60 cm−1, preferably +\−25 cm−1, and most preferably +\−10 cm−1, which corresponds to a peak in the CARS spectrum associated with the C—H vibrations in lipid molecules. The pump and Stokes beams overlapped in a small focal volume, preferably less than 1 $\mu m^3$, within the sample, are scanned across the sample in a same focal plane. In this manner, CARS images of a scanned portion of the sample are obtained, for example in forward and/or epi-direction of detection, where the epi-direction is the direction of backscattering and is opposite to the forward direction. Depending on the sample type, it is readily understood that other wavelengths and frequency differences may be appropriate.

The handheld probe 8 is comprised generally of a scanning mechanism 32, a miniature optics subsystem 33 and a dichroic mirror 34. Each of these components reside in a housing 31 configured to be grasped by the user. The housing 31 includes a barrel 35 protruding from one side of the housing, where the barrel 35 is sized to host the optics subsystem 33 as further described below. The housing 31 further includes two fiber couplings: one for coupling to the laser delivery subsystem 10 and the other for coupling to the collection subsystem 20.

In an exemplary embodiment, the miniature optics 33 operate to focus the excitation beam onto the sample. The optics are designed with the intention of integrating them inside the barrel portion of the handheld probe 8 for in vivo imaging. This imposed the requirement that the distal end of the housing would have a tip whose outer diameter is on the order 3 mm. It is readily understood that the diameter may be decreased or increased depending on the application. This meant that the optics had to be designed with a diameter of less than 2 mm such that it would still provide an NA of ~0.6, working distance of ~400 µm and enable sub-micron resolution imaging. Traditionally, gradient index (GRIN) lenses with relatively high numerical apertures (NA) of 0.5-0.6 have been preferred in multi-photon endoscopy applications, mainly because of their low cost and nearly diffraction-limited image quality. From an optical design analysis, it became clear that the two excitation wavelengths at 800 nm (pump beam) and 1040 nm (Stokes beam) separated by ~200 nm for CARS imaging of lipids, poses a significant challenge in terms of compensating the longitudinal chromatic aberration in the GRIN lenses.

In the exemplary embodiment, the optics subsystem 33 is comprised primarily of a field lens component 36 and a front end objective lens component 37 as seen in FIG. 4. Relay lenses 38 including the field lens 36 are included in the optical design in order to image the MEMS mirror 32 on the back aperture of the miniature objective 37 with a magnification of 5×. The front end objective lens serves to focus the beam tightly as possible onto the sample. Hence, the optics subsystem 33 opted for a miniaturized front end objective that would perform to the required specification. This is indeed very challenging since a large numerical aperture is required from small diameter optics. Each lens component is comprised of multiple lens using a combination glass types, such as SF4, BK7 and FK51, to compensate for the chromatic aberration of the pump and Stokes beams (e.g., at 800 nm and 1040 nm, respectively) and enable the two wavelengths to overlap in space on the sample. The effective NA of the front end objective component is 0.6 and the designed field of view is 100×100 µm with a working distance of 400 µm. Relay lenses 38 are included in the optical design in order to image the MEMS mirror on the back aperture of the miniature objective with a magnification of 5×. Appropriate anti-reflection coatings may be applied on all optics to maximize throughput of excitation and emission light. A focusing element could be included such that the miniature optics subsystem 33 can be moved axially to access different focal planes inside the sample. In the exemplary embodiment, the fully packaged barrel is ~4.1 cm long. A thin glass window seals off the distal end of the barrel thus permitting water immersion. While the sample is shown directly in front of the optics subsystem 33, it is envisioned that the design could be modified for other applications to implement side scanning, for example, on the sides of arterial walls. While the miniature optics subsystem 33 in the exemplary embodiment is designed for focusing pump and Stokes wavelengths to excite and detect CARS signal from lipid molecules, an alternate optics subsystem may be designed to detect CARS signal from water molecules or from the "fingerprint region" corresponding to the spectral region of ~600-1700 cm-1. An alternate dichroic mirror 34 may be designed to transmit the corresponding pump and Stokes wavelengths. In some embodiments, these components are interchangeable depending on the operating mode.

The scanning mechanism 32 receives the excitation signal via fiber optic 9 from the laser delivery subsystem 10. The scanning mechanism 32 functions to direct the excitation signal along a given direction towards the sample 4 and, more particularly, to scan the excitation signal across the sample 4. In the exemplary embodiment, the scanning mechanism 32 is further defined as a mirror actuated in a micro-electro-mechanical system (MEMS), For example, a MEMS scanner is commercially available from Fraunhofer IPMS in Germany. The device consists of a circular silicon plate in gimbal mounting suspended by a total of four torsional spring bars. The reflectivity of the mirror plate is enhanced by a thin layer of aluminum and was measured to be ~80% at 800 nm. This is in excellent agreement with the reflectivity value reported for a bulk aluminum mirror. Based on this measurement of 80% reflectivity at 800 nm, the reflectivity at 1040 nm is expected to be 96% or better (as it would be for a bulk aluminum mirror). Independent resonant oscillation of the mirror plate (fast axis) and the frame (slow axis) itself, is set up by applying a high voltage to the comb electrodes adjacent to the mirror and frame.

To operate the MEMS scanner, a field programmable gate array (FPGA) board 26 (Altera DE2) running a 50 MHz system clock is programmed to sweep from higher frequencies to lower frequencies with a sweep time of 5 s, until it stops at the resonant frequency for each axis. A custom-built voltage amplifier circuit 24 amplifies the rectangular waveform output from the FPGA 26 to drive the MEMS oscillations along the fast and slow axes. When high voltage is applied to both axes, a Lissajous pattern is scanned, with a filling factor determined by the particular ratio of the slow and fast resonant frequencies. An optical scan angle of +/−17 degrees along both axes is obtained by applying 40 V and 70 V, at the resonant frequencies of 1.336 KHz and 16.99 KHz to the slow and fast axis, respectively.

In other embodiments, laser scanning is achieved by means of cantilever fiber-scanners although MEMS scanners operating at resonant frequencies offer the advantages of adjustable and fast frame rates and allow batch fabrication. Other scanning mechanisms, such as optical fibers surrounded by (or mounted on) piezoelectric actuators, are also contemplated by this disclosure.

The dichroic mirror 34 is disposed between the scanning mechanism 32 and the optics subsystem 33. The dichroic mirror 34 receives emissions resulting from nonlinear interaction of the excitation signal with the sample in a backward direction via the optics subsystem 33 from the sample as shown and directs the emission signal to the collection subsystem 20. The dichroic mirror 34 is an important component of an epi-detection multimodal endoscope system 6 because it will only transmit the excitation wavelengths of pump and Stokes, but block the strong non phase-matched FWM contribution generated inside the delivery fiber 9. The emission may be directed at a 90 degree angle from the direction of the excitation signal as shown in FIG. 3. In an alternative arrangement, a reflective component 51 is incorporated along the collection path to direct the emission in a direction opposite the direction of the excitation signal as shown in FIG. 5. Other arrangements, including collecting the emission in a forward direction, are contemplated within the broader aspects of this disclosure. In any case, the emission is directed through a collection fiber 52 that couples the probe 8 to the collection subsystem 20.

With continued reference to FIG. 3, the collection subsystem 20 may include a detector 22, a drive circuit 24 for the scanning mechanism 32, a field-programmable gate array 26 (FPGA) and a computer 28. Emission signal from the sample 4 is collected with the collection fiber 52 and directed towards the detector 22. The detector 22 may be followed by an amplifier-discriminator unit (e.g., Ortec 9327). In the exemplary embodiment, the detector 22 is further defined as a photomultiplier tube (PMT). An avalanche photodiode (APD) or an intensified CCD camera may also serve as the detector 22. TTL pulses from the discriminator are sent to the FPGA 26 where they are synchronized with respect to the FPGA clock. The time difference between subsequent events is encoded and sent to the computer 28 via a custom-made board that uses the FT2232H chip. A program running on the computer receives these data and saves them to disk. An image reconstruction program simulates the trajectory of the laser and creates a mapping table. It uses the stored data files in the computer 28 and transforms the scanned vector data in a frame period into a 512×512 pixel image. The phase delay between the driving electrical signal and the mechanical response of the MEMS mirror is adjusted in order to remove ghost images in the final 512×512 pixel image.

Depending upon the operating mode, signal from the collection fiber 52 will be filtered so that excitation wavelengths are blocked. Furthermore, appropriate band pass filters are applied to allow only the applicable CARS signal, TPEF signal, SHG signal, or THG signal to reach the detector 22. Thus, different types of filters are selectively applied to correlate to the operating mode. For example, a 65 nm bandpass filter centered at 645 nm can be used in the collection beam path to selectively pass only the CARS signal. Suitable filters for the different modes are readily understood by those skilled in the art.

Frame rates that are achievable with the exemplary endoscope system are further described. The goal is to achieve a self repeating Lissajous scan pattern of the optical beam that fulfills the conditions that i) every pixel in the 512×512 pixel image is hit at least once and ii) the spatial coverage is very uniform across the FOV. First experimentally measure the resonance curves for the slow and fast axes at 40 V and 70 V, respectively. From this data, determine the resonant frequencies for the desired optical scan amplitude. These slow and fast axis resonant frequencies are then expressed in terms of the number of system clock cycles (ticks), ns and nf, respectively, where the system clock of the FPGA is at a much higher frequency of 50 MHz. The resulting Lissajous pattern will self repeat after n ticks where n is the least common multiple of ns and nf. Thus the frame repeat rate is given by (50 MHz)/n. It should be clear that different choices of ns and nf, or in other words, the slow and fast axis resonant frequencies, will give different frame repeat rate. The choice of the slow and fast axis resonant frequencies of 1.429 KHz and 17.225 KHz, respectively provided a good spatial coverage over a 512×512 pixel image. The resulting frame rate of 4 Hz is sufficient for our current requirement of imaging stationary samples. This frame rate was identical for all imaging modalities in the system. A fixed amount of data (10 MB, roughly 9 million nonlinear optical events) is collected per image file which included multiple frames. The brighter images had more nonlinear optical events per frame, and therefore the time required to acquire this data was less.

The resolving power of the endoscope was investigated by acquiring transmission images of a USAF resolution test target (Edmund Optics). The femtosecond pulsed laser tuned to 720 nm, followed the pump beam path. A water drop was placed on top of the tip of the barrel and the USAF target glass slide was placed facing down, touching this water drop such that the smallest features on the target were centered on the focused beam spot with a reduced average power of 1.5 mW. The smallest element in the group has a line spacing of 228 line pairs/mm, corresponding to a line width of approximately 2.2 µm. There is no distortion in the shape of the individual lines in the image except for a conical distortion in which the right side of the image is slightly rotated counter clockwise. This is a known artifact due to the 45 degree angle between the slow axis of the MEMS mirror and the incident light beam and can be corrected with image post processing.

Next, TPEF microscopy was performed on a sample of diluted solution of 1 µm fluorescent microspheres (Polysciences Inc., PA, USA). Light from the femtosecond laser at 800 nm was reflected off the MEMS with close to 80% reflectivity and ~64% of this light was transmitted through the optics inside the barrel, such that an average power of ~28 mW is focused at the sample. Most of the 1 µm spheres are seen to coalesce together, however a few individual spheres can be clearly resolved. The intensity profile is plotted for such individual 1 µm fluorescent spheres that are in focus across the FOV. The average value of the full width at half-maximum of the Gaussian curve fitted to the intensity profile gives the value of the lateral resolution and this is determined to be ~1.3 µm for the multimodal miniature endoscope system 6. This is in good agreement with the design value of 1 µm.

For CARS imaging experiments, a small drop of diluted solution of 20 µm and 4.5 µm polystyrene beads on a #1 cover slip was used. The pump beam at 800 nm and the Stokes beam containing the near IR filtered output at 1057 nm are focused into the volume of beads, so that the aromatic CH vibration in polystyrene at 3045 $cm^{-1}$ Raman shift gets resonantly excited. The CARS image of the 20 µm spheres was obtained with the endoscope system when the average power at the sample was ~28 mW in the pump beam and ~0.8 mW in the Stokes beam. From this image it was seen that the FOV is ~70×70 µm. The slightly decreasing intensity to the right of the FOV is because of slight beam clipping owing to the non-perfect alignment of the barrel with respect to the MEMS mirror on the vertical rail. The axial resolution of the endoscope system was experimentally measured by CARS imaging of 4.5 µm polystyrene beads (Polysciences Inc.) in steps of 1 µm along the "z" optical axis. The maximum intensity values of the line profiles in the z stack were plotted as a function of z step. A full width at half-maximum value of the Gaussian curve fitted to this plot resulted in an axial resolution of 12.74 µm for the endoscope system 6. This is larger than the design value of 3 µm and is mainly attributed to residual chromatic aberration inside the miniature objective as well as slight optical misalignment in the beam paths of the bench top microscope system.

Next, multimodal ex vivo imaging of biological tissue samples was demonstrated with the endoscope system 6. A 0.5 mm thin section of a fixed dorsal root from a YFP mouse (Jackson Laboratory, Bar Harbor, Me.) was mounted on a slide, covered with a thin cover slip and imaged facing down for TPEF and CARS, as described above. In this sample, the axons selectively express yellow fluorescent protein (peak emission≈530 nm) whereas the lipid rich myelin surrounding the axons is label-free. The frequency difference between the pump and Stokes light sets up a coherent vibration of the CH bonds at 2845 $cm^{-1}$ Raman shift in the lipid molecules of myelin. A 65 nm bandpass filter centered at 645 nm (Chroma Technology) is used in the collection beam path to selectively pass only the CARS signal. The result was a CARS image having unlabeled myelin surrounding the axons. This confirms that the contribution due to YFP emission at 645 nm is negligible and that the image is primarily due to CARS emission.

The excitation wavelength for optimal two photon absorption in YFP is known to be ~970 nm. In the exemplary embodiment, the laser could only be tuned to ~870 nm where mode locking was still possible. The TPEF image of the same sample of fixed YFP mouse dorsal root was obtained at 870 nm. Although the signal to noise ratio is poor, the YFP labeled axons can be identified. The laser was tuned back to 800 nm for SHG imaging and a short pass filter (Chroma Technology, VT, USA) was used in the collection beam path to selectively pass only wavelengths below 450 nm. The wavy type-I collagen fibers are well resolved in the resulting image.

In the embodiment set forth above, the excitation light is scanned in a Lissajous pattern by means of a two dimensional scanning MEMS mirror that is 500 µm in diameter and is focused on the sample by a miniaturized probe containing miniature relay optics and a multiple lens objective that is 1.8 mm in diameter. The miniature objective corrected for chromatic aberration is able to generate a strong CARS signal corresponding to the vibrations of the CH bonds at 2845 $cm^{-1}$ and 3045 $cm^{-1}$ Raman shifts. Proof of principle images of fluorescent and polystyrene beads as well as biological tissue obtained with the setup demonstrate very high resolution and the shapes of features remain consistent throughout the FOV.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A miniaturized multi modal imaging system, comprising:

A miniaturized multi modal imaging system,
a laser delivery subsystem operates to generate an excitation signal in one of two forms, a first form having a pump beam and a second form having a pump beam combined with a Stokes beam, where the laser delivery subsystem includes a first prechirp unit disposed in the pump path and operable to compensate the pump beam for dispersion;

a second prechirp unit disposed in the Stokes path and operable to compensate the Stokes beam for dispersion; and an optical element configured to receive both the pump beam and the Stokes beam and operates to form the excitation signal from the pump beam and Stokes beam a scanning mechanism configured to receive the excitation signal and operates to direct the excitation signal in a given direction towards a sample;

an optics subsystem configured to receive the excitation signal from the scanning mechanism and focus the excitation signal onto the sample, wherein the optics subsystem includes a field lens, a front end objective lens and at least one relay lens interposed between the field lens and the front end objective lens, such that the relay lens images the excitation signal from the scanning mechanism onto the front end objective lens and each lens is comprised of at least two different types of glass which operate to compensate for chromatic aberration in the excitation signal;

an optical fiber that optically couples the laser delivery subsystem to the scanning mechanism;

a detector configured to receive an emission resulting from non-linear interaction of the excitation signal with the sample; and a dichroic mirror disposed between the scanning mechanism and the optics subsystem, the dichroic mirror configured to receive the emission from the sample in a direction opposite the given direction and direct the emission along a collection path to the detector; and a controller interfaced with the laser delivery subsystem, wherein the controller, in a first mode, controls the laser delivery subsystem to output an excitation signal having only a pump beam and, in a second mode, controls the laser delivery subsystem to output an excitation signal having a pump beam combined with a Stokes beam.

2. The imaging system of claim 1 wherein the laser delivery subsystem having a single femtosecond laser source tunable to different wavelengths and an optical beam splitter configured to receive an excitation signal from the laser source and divide the excitation signal into the pump beam along a pump path and the Stokes beam along a Stokes path.

3. The imaging system of claim 2 further comprises a first filter configured to receive the emissions from the sample and the system operates in a first mode such that the laser source is tuned to a first wavelength.

4. The imaging system of claim 3 further operates in a second operating mode such that the laser source is tuned to a second wavelength that is different than the first wavelength.

5. The imaging system of claim 3 further comprises a second filter configured, in the second operating mode, to receive the emissions from the sample, the second filter being different than the first filter.

6. The imaging system of claim 1 wherein the scanning mechanism is further defined as a mirror actuated in a micro-electro-mechanical system.

7. The imaging system of claim 1 wherein the detector is further defined as a photomultiplier tube.

8. The imaging system of claim 1 is further defined as an endoscope or a microscope.

9. The imaging system of claim 1 further comprises a collection fiber interposed between the dichroic mirror and the detector and configured to receive the emission from the dichroic mirror.

10. A miniaturized multi modal imaging system, comprising:

a laser delivery subsystem having a single femtosecond laser source configured to generate an excitation signal selected from a group consisting of: a first form having a pump beam only and a second form having a pump beam combined with a Stokes beam, where the laser delivery subsystem includes an optical beam splitter configured to receive the excitation signal and divide the excitation signal into a pump beam along a pump path and a Stokes beam along a Stokes path;

a first prechirp unit disposed in the pump path and operable to compensate the pump beam for dispersion;

a second prechirp unit disposed in the Stokes path and operable to compensate the Stokes beam for dispersion; and an optical element configured to receive both the pump beam and the Stokes beam and operates to form the excitation signal from the pump beam and Stokes beam;

a scanning mechanism configured to receive the excitation signal and operates to direct the excitation signal in a given direction towards a sample;

an optics subsystem configured to receive the excitation signal from the scanning mechanism and focus the excitation signal onto the sample, wherein the optics subsystem includes a field lens, a front end objective lens and at least one relay lens interposed between the field lens and the front end objective lens, such that the relay lens images the excitation signal from the scanning mechanism onto the front end objective lens and each lens is comprised of at least two different types of glass which operate to compensate for chromatic aberration in the excitation signal;

an optical fiber that optically couples the excitation signal from the laser delivery subsystem to the scanning mechanism;

a detector configured to receive emission resulting from non-linear interaction of the excitation signal with the sample;

a dichroic mirror disposed between the scanning mechanism and the optics subsystem, the dichroic mirror configured to receive emission from the sample in a direction opposite the given direction and direct the emission along a collection path to the detector; and a controller interfaced with the laser delivery subsystem, wherein the controller, in a first mode, controls the laser delivery subsystem to output an excitation signal having only a pump beam and, in a second mode, controls the laser delivery subsystem to output an excitation signal having a pump beam combined with a Stokes beam.

11. The imaging system of claim 10 further comprises a first filter configured to receive the emissions from the sample and the system operates in a first mode such that the laser source is tuned to a first wavelength.

12. The imaging system of claim 11 further operates in a second operating mode such that the laser source is tuned to a second wavelength that is different than the first wavelength.

13. The imaging system of claim 12 further comprises a second filter configured, in the second operating mode, to receive the emissions from the sample, the second filter being different than the first filter.

14. The imaging system of claim 10 wherein the optical element is further defined as a dichroic mirror.

15. The imaging system of claim 10 wherein the scanning mechanism is further defined as a mirror actuated in a micro-electro-mechanical system.

16. The imaging system of claim 10 wherein the optics subsystem is housed in a barrel having an outer diameter on the order of three millimeters.

17. The imaging system of claim 10 wherein the detector is further defined as a photomultiplier tube.

18. The imaging system of claim 10 further comprises a probe configured to be grasped by a user, wherein the probe houses the scanning mechanism, the optics subsystem and the dichroic mirror.

\* \* \* \* \*